United States Patent [19]

Barabas

[11] Patent Number: 4,851,543

[45] Date of Patent: Jul. 25, 1989

[54] WATER SOLUBLE MULTICOMPLEX OF AMINOBENZOIC ACID

[75] Inventor: Eugene S. Barabas, Watchung, N.J.

[73] Assignee: GAF Corporation, Wayne, N.J.

[21] Appl. No.: 150,957

[22] Filed: Feb. 1, 1988

Related U.S. Application Data

[62] Division of Ser. No. 858,778, May 2, 1986, Pat. No. 4,758,674.

[51] Int. Cl.$^4$ ............................................. C07D 207/12
[52] U.S. Cl. ..................... 548/519; 548/523; 548/524; 424/80; 524/240
[58] Field of Search ................... 548/519, 524; 424/80

[56]  References Cited

U.S. PATENT DOCUMENTS

| | | | |
|---|---|---|---|
| 2,691,619 | 10/1954 | Bavley | 424/80 |
| 2,918,411 | 10/1959 | Hill | 424/80 |
| 3,671,545 | 6/1972 | Halpern | 424/80 |
| 4,684,519 | 8/1987 | Barabas | 424/80 |
| 4,704,436 | 11/1987 | Barabas | 424/80 |
| 4,713,238 | 12/1987 | Barabas | 424/80 |

OTHER PUBLICATIONS

Molyneux and Frank, "Interaction of [PVP] with Aromatic Compd...", Aug. 15, 1961, JACS, vol. 83, #15, pp. 3169-etc.
Merck Index "Povidone", Povidone-Iodine, p. 1106, 10th ed., 1983.

*Primary Examiner*—Anton H. Sutto
*Assistant Examiner*—Frederick Tsung
*Attorney, Agent, or Firm*—Marilyn J. Maue; Joshua J. Ward

[57]  ABSTRACT

The invention relates to a novel water soluble aminobenzoic acid in a complexed state which is derived from the reaction between a poly(N-vinyl-2-pyrrolidone)-halogen complex and an aminobenzoic acid and to the process for the preparation of said multicomplex.

4 Claims, No Drawings

WATER SOLUBLE MULTICOMPLEX OF AMINOBENZOIC ACID

This is a division of application Ser. No. 858,778, filed May 2, 1986. U.S. Pat. No. 4,758,674.

The meta- ortho- and para-amino benzoic acids are well known and are used as dye intermediates, pharmaceuticals, vitamin adducts and nutritional substances for verterinary use. However, administration of this compound is complicated by its extreme water-insolubility. Because of its application in pharmaceutical areas, it is important that no solvent having toxic or other deleterious side effects be employed for its medicinal use in solution.

Accordingly, it is an object of the present invention to provide aminobenzoic acid in a highly water soluble form with no objectionable side effects.

Another object of this invention is to provide a commercially feasible process for the production of an aminobenzoic acid in highly water soluble form.

Another object is to provide an aminobenzoic acid complex of increased medicinal properties.

These and other objects of the invention will become apparent from the following description and disclosure.

According to this invention there is provided a aminobenzoic acid complexed water soluble product derived from the reaction between a poly(N-vinyl-2-pyrrolidone)-halogen complex and an aminobenzoic acid. This product is a true complex containing repeating units of the structures A and B believed to contain hydrogen bonding as shown below.

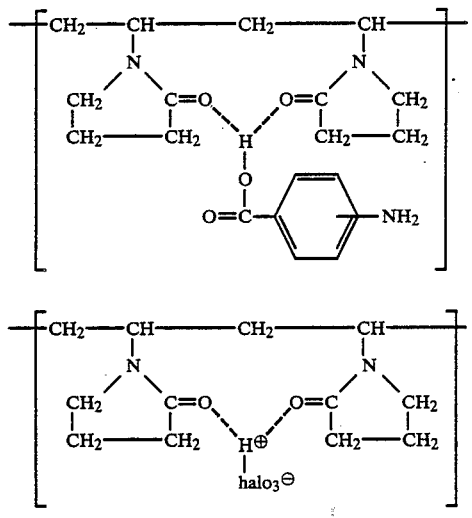

wherein halo is iodine, chlorine or bromine, iodine being preferred.

However, it is to be understood that hydrogen bonding explains only one of the possible structures which can be attributed to the complex. For example, hydrophobic bonding, as well as bonding by various forms of Van der Waals forces can be present to either a major or minor extent in the complex.

There is no intention to be restricted in the scope of this invention by theoretical considerations with respect to the nature of the complex bonding since it will be recognized that the ability of the compound to be complexed and solubilized by poly(vinylpyrrolidone) depends to a great extent upon the chemical, physical and morphological characteristics of the compound, the hydrophilic/hydrophobic ratio of its structural elements, the nature and relative position of the substituents, the bulkiness of the molecule in general and the substituents in particular. Slight differences in any of the above factors may significantly alter the solubilizing capability. For instance p-aminobenzoic acid forms a very water soluble complex with polyvinylpyrrolidone. Conversely, the structurally similar p-dimethylamino benzoic acid does not form a water soluble adduct with polyvinylpyrrolidone. Thus, the desired solubility of a complex cannot be predicted solely on chemical similarities. Each compound must be viewed and tested individually and its performance will depend upon the combination of the aforesaid parameters of the compound to be complexed.

The complexed product of this invention may also contain non-complexed sites, such as

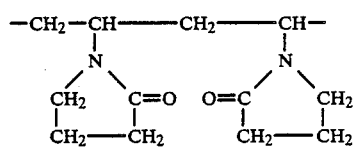

The poly(N-vinyl-2-pyrrolidone)-halogen complex reactant of this invention can be prepared according to the process disclosed in my copending application Ser. No. 849,918, FDN-1374, filed Apr. 9, 1986 and entitled METHOD OF PREPARING A POLYVINYLPYRROLIDONE-HALOGEN COMPLEX; although other convenient processes for the preparation are known and can be employed to provide the complexed polymeric reactant in the present invention. The mole ratio of halogen to poly(N-vinyl-2-pyrrolidone) in the complex is generally between about 1:3 and about 1:15, preferably 1:8–12 so that the polymer contains a significant number of non-complexed sites on which additional complexing can occur. The poly(N-vinyl-2-pyrrolidone)-halogen complex reactant of this invention can have a number average molecular weight between about 5,000 and about 150,000; between 15,000 and 50,000 being preferred.

The aminobenzoic acids employed herein include the o-, m- and p-species which are reacted with the poly(N-vinyl-2-pyrrolidone)-halogen complex to produce a multicomplexed polymer which in addition to repeating units of A and B, may also contain uncomplexed units of the formula

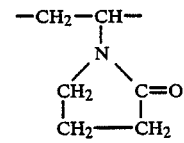

The complexed units, and any non-complexed units, which may be present in the polymer may occur in block, random or alternating distribution. In any case, the resulting product contains at least 8 wt. % complexed units, and up to 30 wt. % complexed units of the aminobenzoic acid moiety; and at least 12 wt. % up to at least 15 wt. % complexed units of the halogen, e.g. iodine, moiety in the product, so as to retain properties associated with the aminobenzoic acid while additionally providing the medicinal properties of the complexed iodine moiety. The multicomplexed state of the aminobenzoic acid of this invention has been established by experiment showing that a gradual dilution of from 2% to 0.01% in water, no free aminobenzoic acid precipitated from the aqueous solution. If the aminobenzoic acid had not been complexed, it would have precipitated out of solution at a dilution within this range. A complex water solubility of at least 15% is desired and water solubility as high as 25% has been achieved. That the material remains in solution at high dilution, significantly above the solubility limit of uncomplexed aminobenzoic acid i.e. 0.5% at room temperature, is indeed unexpected.

While the complexes of the invention are stable under normal conditions, they are subject to in vivo hyrolytic forces and other physical chemical effects which lead to slow dissociation. Therefore these complexes can function as slow release systems suitable for the sustained delivery of the drug portion of the complex in medical and verterinarial applications.

Generally, the aminobenzoic acid in the multicomplexed state of this invention exhibits at least a 50 fold increase in water solubility.

The aminobenzoic multicomplex is prepared by a relatively simple and direct process which involves dissolving both the aminobenzoic acid and the poly(N-vinyl-2-pyrrolidone)-halogen complex in a $C_1$-$C_5$ alcohol, preferably ethanol, to produce between about 5 and about 25 weight % solutions of each reactant. More often solutions of from about 8% to about 15% by weight of active components are recommended. The solutions are then combined in a weight ratio of iodine complex to acid of between about 1:1 and about 10:1, preferably in a ratio of 4–7:1, and thoroughly mixed under atmospheric pressure, or superatmospheric pressure up to 50 psig, at a temperature above 3° C. and below the boiling point of the alcohol solvent, which includes a range of between about 4° C. and about 100° C., preferably between about 10° C. and about 40° C. The mixture is agitated under these conditions for a period of from about 5 minutes to about 3 hours. Usually between about 10 and about 30 minutes is sufficient to effect the complexing reaction.

After completion of the reaction the resulting mixture comprising a liquid alcohol phase and a solid multicomplexed product phase is treated to remove solvent by any conventional means, such as rotary evaporation or freeze drying. Evaporation is conducted in vacuo, e.g. under a pressure of from about 2 to about 40 mm Hg, preferably not more than 20 mm Hg. The remaining solids are recovered and dried at a temperature between about 45° C. and about 100° C., preferably between about 50° C. and about 65° C. for a period of 1 to 24 hours.

The dried product of the process is readily dissolved in water and the water solubility of the aminobenzoic acid in this multicomplexed form is increased from about 0.3% to at least 25% at room temperature.

Having thus generally described the present invention, reference is now had to the following examples which illustrate preferred embodiments but which are not to be construed as limiting to the scope of the invention as more broadly set forth hereinabove and in the appended claims.

EXAMPLE 1

A. Preparation of Poly(N-vinyl-2-pyrrolidone)-iodine Complex

A 35% poly(N-vinyl-2-pyrrolidone) in aqueous solution was made up. A separate ethanol solution of iodine and hydriodic acid, in a mole ratio of 4:1 was separately prepared. Into a 5 liter, 4-necked flask equipped with a mechanical stirrer, a reflux condenser and a thermometer, was introduced 2214.0 grams of the aqueous polymer solution. The solution was heated to 85° C., whereupon 789.0 grams of 20% iodine in ethanol and 68.6 grams of 56% hydriodic acid was added over a 2 minute period. The resulting mixture was stirred at 85° C. for 90 minutes to form the poly(N-vinyl-2-pyrrolidone)-iodine complex. The flask was then equipped with a Liebig condenser and distilled to remove the ethanol-water azeotrope at a temperature increasing from 85° C. to 90° C. During distillation, distilled water was added so as to maintain the solid complexed product in the reaction mixture at about 24%.

After 90 minutes, the distilland was cooled below 40° C. and the condenser was attached to a vacuum source through 3 acetone-dry ice traps. Remaining azeotrope was then removed at 38°–39° C. under 55 mm/Hg pressure. The remaining poly(N-vinyl-2-pyrrolidone)-iodine complexed solution was cooled to room temperature and deionized water (1800 grams) was added. The solution was fed to a spray dryer from a graduated dropping funnel, said spray dryer operating at 5.4 Kg/cm$^2$ air pressure; inlet air temperature between 270° and 280° C.; outlet air temperature between 105° and 125° C. and feed rate of 15 mils per minute. The available iodine of the spray dryed complexed product was 11.89%.

B. Preparation of Poly(N-vinyl-2-pyrrolidone)-iodine-p-aminobenzoic Double Complex 100 grams of p-aminobenzoic acid were dissolved in 1,000 grams of ethanol and 100 grams of poly(N-vinyl-2-pyrrolidone)-iodine complex from part A was separately dissolved in 1,000 grams of ethanol. These solutions were introduced into separate dropping funnels from which 100 grams of p-aminobenzoic acid solution and 400 grams of the iodine complex solution was introduced dropwise in a period of about 20 minutes into a 1,000 milliliter flask and mixed for a period of about 15 minutes at room temperature. The flask was then placed on a rotary evaporator and ethanol solvent was removed in vacuo (about 20 mm Hg). The remaining solid multicomplexed compound was then dried in a vacuum oven in vacuo at 60° C. for 6 hours. The multicomplexed product contained 20% by wt. of p-aminobenzoic acid.

EXAMPLE 2

Water Solubility of the Double Complex 65 grams of the poly(N-vinyl-2-pyrrolidone)-iodine-p-aminobenzoic acid double complex was placed in a screwcap jar and agitated with 35 grams of distilled water in a horizontal shaker at room temperature for one hour after which a viscous solution was obtained. The solution was allowed to stand at room temperature for an additional 5 hours during which time bubbles entrained during the shaking operation disappeared. It was noted that all of the solids went into solution and the solution contained 13 grams of p-aminobenzoic acid, corresponding to a 27.1% solubility of the para-aminobenzoic acid moiety.

As a control, the solubility of uncomplexed p-aminobenzoic acid in water was found to be 0.3%.

EXAMPLE 3

Preparation of Poly(N-vinyl-2-pyrrolidone)-iodine-o-aminobenzoic Acid Double Complex The procedure in Example 1 parts A and B were repeated except that o-aminobenzoic acid was substituted for p-aminobenzoic acid.

The double complexed product recovered after drying in the vacuum oven was subjected to the solubility test described in Example 2. The amount of o-aminobenzoic acid dissolved in the form of the double complex was 13 grams corresponding to 27.1% solubility in water.

As a control, the solubility of the uncomplexed o-aminobenzoic acid in water was tested and found to be 0.5%.

Examples 1–3 are intended to set forth preferred embodiments of the present invention; however, many variations and modifications of the above experiments and complexed products will become apparent from the foregoing description and disclosure. For example, other alcohol solvents can be employed for the reacting species as well as other poly(N-vinylpyrrolidone)-halogen complexes such as the bromine or chlorine complex to provide multicomplexes wherein the aminobenzoic acid shows markedly increased water solubility.

EXAMPLE 4

Comparative Example

The procedure in Example 1 was repeated except that p-dimethylamino benzoic acid was substituted for p-amino-benzoic acid.

The adduct recovered after drying was subjected to the solubility test described in Example 2 by dissolving 2 grams of adduct in 20 grams of distilled water. However, the material failed to dissolve even after it was further diluted by the addition of another 20 grams of distilled water.

What is claimed is:

1. The process for producing the multicomplexed compound of poly(N-vinyl-2-pyrrolidone)-halogen complex and an aminobenzoic acid which comprises: mixing alcoholic solutions of an aminobenzoic acid and a poly(N-vinyl-2-pyrrolidone)-halogen complex having repeating units of

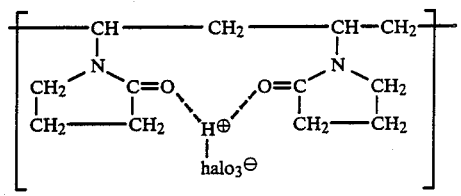

and repeating units of

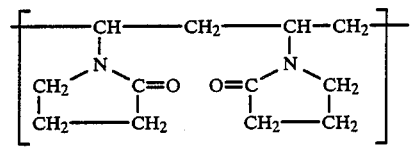

wherein halo is iodine, bromine or chlorine, in a mole ratio of aminobenzoic acid to poly(N-vinyl-2-pyrrolidone)-halogen complex is between about 1:1 and about 1:10, agitating the mixture under a pressure of from about atmospheric to about 50 psig at a temperature of from about 4° C. to about 100° C. and below the boiling point of said alcohol, for a period of from about 5 minutes to about 3 hours, to form a liquid solvent phase and a solid multicomplexed product phase, separating said solvent from said multicomplexed product, drying said complexed product and recovering the dried solid as the multicomplexed product of the reaction.

2. The process of claim 1 wherein the poly(N-vinyl-2-pyrrolidone)-halogen complex is poly(N-vinyl-2-pyrrolidone)-iodine in which the polymer has a molecular weight of from about 5000 to about 150,000.

3. The process of claim 2 wherein the poly(N-vinyl-2-pyrrolidone)-iodine complex has a molecular weight between about 15,000 and about 50,000 and said complex contains from about 8% to about 12% available iodine.

4. The process of claim 2 wherein the poly(N-vinyl-2-pyrrolidone)-iodine complex solution is mixed with the aminobenzoic acid solution in a weight ratio of between about 4:1 and about 7:1 and wherein the mixture is heated to a temperature of from about 10° C. to about 40° C. under a pressure of from about 14 to about 50 psig.

* * * * *